US006950757B2

(12) United States Patent
Stewart

(10) Patent No.: US 6,950,757 B2
(45) Date of Patent: Sep. 27, 2005

(54) SCREENING METHODS FOR IDENTIFYING LIGANDS

(75) Inventor: Lansing J. Stewart, Bainbridge Island, WA (US)

(73) Assignee: Emerald BioStructures, Inc., Bainbridge Island, WA (US)

(*) Notice: Subject to any disclaimer, the term of this patent is extended or adjusted under 35 U.S.C. 154(b) by 379 days.

(21) Appl. No.: 10/121,094

(22) Filed: Apr. 11, 2002

(65) Prior Publication Data

US 2002/0197628 A1 Dec. 26, 2002

Related U.S. Application Data

(60) Provisional application No. 60/283,045, filed on Apr. 11, 2001.

(51) Int. Cl.[7] .......................... B01D 9/02; G01N 31/00; C12Q 1/68
(52) U.S. Cl. .............................. 702/27; 435/6; 435/7.1; 117/11
(58) Field of Search ........................ 702/27, 19; 435/6, 435/7.1; 117/11; 585/817

(56) References Cited

U.S. PATENT DOCUMENTS

| | | | | |
|---|---|---|---|---|
| 5,130,105 A | 7/1992 | Carter et al. | ................... | 22/215 |
| 6,039,804 A | 3/2000 | Kim et al. | ................... | 117/206 |
| 6,130,227 A | 10/2000 | Merlini et al. | .............. | 514/283 |
| 6,267,935 B1 | 7/2001 | Hol et al. | ................ | 422/245.1 |
| 6,297,021 B1 | 10/2001 | Nienaber et al. | ............ | 435/7.1 |

FOREIGN PATENT DOCUMENTS

| WO | WO 99/45379 | 9/1999 |
|---|---|---|
| WO | WO 01/88113 | 11/2001 |

OTHER PUBLICATIONS

Bernstein B., et al., "A bisubstrate analog induces unexpected conformational changes in phosphoglycerate kinase from *Trypanosoma brucei*," *Journal of Molecular Biology*, vol. 279, p. 1137–1148 (1998).
Bernstein B., et al., "Synergistic effects of substrate–induced conformational changes in phosphoglycerate kinase activation," *Nature*, vol. 385 p. 275–278 (1997).
Brünger A, et al., "Crystallography and NMR systems (CNS) A new software system for macromolecular structure determination," *Acta Crystallographica*, Section D, vol. D54, p. 905–921 (1998).
Burgin A., et al., "A novel suicide substrate for DNA topoisomerases and site–specific recombinases," *Nucleic Acids Research*, vol. 23, p. 2973–2979 (1995).
Champoux J., "DNA Topoisomerases: structure, function, and mechanism," *Annual Reviews Biochem*, vol. 70 p. 369–413, (2001).
Chen A., et al., "DNA topoisomerases: Essential enzymes and lethal targets," *Annu. Rev. Pharmacol. Toxicol*, vol. 34, p. 191–218 (1994).

Hampton Research Solutions for Crystal Growth, Crystal Screen Reagent Formulations, listing PDF, 3pp, Downloaded from Hampton Research Website http://www.hamptonresearch.com/hrproducts/2110.html on World Wide Web URL: http://www.hamptonresearch.com/hrproducts/2110.html.
Hertzberg R., et al., "On the mechanism of topisomerase I inhibition by camptothecin: evidence for binding to an enzyme–DNA complex," *Biochemistry*, vol. 28 p. 4629–4638 (1989).
Hsiang Y., et al., "Camptothecin induces protein–linked DNA breaks via mammalian DNA Topoisomerase I." *The Journal of Biological Chemistry*, vol. 260, p. 14873–14878, (1985).
Huang H., et al., "Structure of a covalently trapped catalytic complex of HIV–1 reverse transcriptase: implications for drug resistance," *Science*(1998), 282, p. 1669–1675.
Jia Z., et al., "Structure of protein tyrosine phosphatase 1B in complex with inhibitors bearing two phosphotyrosine mimetics," *Journal of Medicinal Chemistry*, vol. 44, p. 4584–4594 (2001).
McRee D., "XtalView/Xfit—A Versatile Program for Manipulating Atomic Coordinates and Electron Density," *Journal of Structural Biology*, vol. 125, p. 156–165 (1999).
Navaza J., "AMORE: a automated package for molecular replacement," *Acta. Crystallogrphica*, vol. A50, p. 157–163 (1994).
Nitiss J., et al., "DNA topoisomerase–targeting antitumor drugs can be studied in yeast," *Proc. Natl. Acad. Sci. U.S.A.*, vol. 85, p. 7501–7505 (1988).
Redinbo M., et al., "Crystal structures of human topoisomerase 1 in covalent and noncovalent complexes with DNA," *Science*, vol. 279, p. 1504–1513 (1998).
Scapin G., et al., "The structure of apo protein–tyrosine phosphatase 1B C215S mutant: more than just an S→ O change," *Protein Science*, vol. 10, p. 1596–1605 (2001).
Stewart L., et al., "Reconstitution of human topoisomerase 1 by fragment complementation." *J Mol Biol*, vol. 269, p. 355–372 (1997).
Stewart L., et al., "High–throughput crystallization and structure determination in drug discovery," *Drug Discovery Today*, vol. 7, 187–196 (2002).
Stewart L., et al., "Biochemical and biophysical analyses of recombinant forms of human topoisomerase 1," *The Journal of Biological Chemistry*, vol. 271, p. 7593–7601 (1996).
Stewart L., et al., "A model for the mechanism of human topoisomerase 1," *Science*, vol. 279, p. 1534–1541 (1998).
Wall M., et al., "The isolation and structure of camptothecin, a novel alkaloidal leukemia and tumor inhibitor from Camptotheca acuminata," *Journal of the American Chemical Society*, vol. 88, p. 3888–3890 (1966).

*Primary Examiner*—Marjorie A. Moran
(74) *Attorney, Agent, or Firm*—Christensen O'Connor Johnson Kindness PLLC

(57) ABSTRACT

This invention relates to crystallization based assays for identifying ligands that bind to a macromolecule.

5 Claims, No Drawings

SCREENING METHODS FOR IDENTIFYING LIGANDS

CROSS-REFERENCE TO RELATED APPLICATIONS

This application claims benefit of U.S. provisional patent application No. 60/283,045, filed Apr. 11, 2001.

STATEMENT OF GOVERNMENT INTEREST

This invention was made with Government support under contract nos. R43CA79439-01, R43CA82964-01 and R43CA79439-02 awarded by the National Cancer Institute. The Government may have certain rights in the invention.

FIELD OF THE INVENTION

This invention relates to screening methods for identifying ligands of a macromolecule.

BACKGROUND OF THE INVENTION

Pharmaceuticals can be developed from lead compounds that are identified through a random screening process directed towards a macromolecule, such as a nucleic acid or a protein receptor. Large scale screening approaches can be complicated by a number of factors. First, many assays are laborious or expensive to perform. Assays may involve experimental animals, cell lines, or tissue cultures that are difficult or expensive to acquire or maintain. These considerations often place practical limitations on compounds that reasonably can be screened.

U.S. Pat. No. 6,297,021 describes ligand screening processes that rely on identification by X-ray crystallography of ligands binding to a macromolecule crystal. The use of X-ray crystallography in the identification of ligand binding is a tedious and slow process that requires expensive equipment that must be run by highly skilled operators.

Thus, those employing known screening methods are frequently forced to limit their search to those compounds for which some prior knowledge suggests that the compounds are likely to be effective and/or are required to utilize tedious analysis techniques requiring high operator skill levels. These strategies limit the range of compounds tested, and many useful drugs may be overlooked.

There exists a continuing need, therefore, for new screening methods that can identify ligands to a target of interest.

SUMMARY OF THE INVENTION

In one embodiment, this invention relates to a process for identifying a ligand which binds to a macromolecule comprising: providing a solution containing a macromolecule; exposing the solution to a potential ligand; and observing whether crystallization of the macromolecule occurs, wherein the macromolecule forms crystals only when bound to a ligand, and wherein formation of crystals indicates binding between the macromolecule and the potential ligand.

In another embodiment, this invention relates to a process for identifying a ligand which binds to a macromolecule comprising: providing a crystal of a macromolecule; exposing the crystal to a potential ligand; and observing whether crystal cracking occurs, wherein cracking of the crystal after exposure to the potential ligand indicates binding between the potential ligand and the macromolecule.

DETAILED DESCRIPTION OF CURRENT EMBODIMENTS

This invention relates to screening methods for identifying ligands that bind to a macromolecule.

The macromolecule or target used in the assays of the invention can encompass proteins, polypeptides, nucleic acids, nucleoproteins or any other suitable macromolecule that is isolated from natural sources or by recombinant methods from any suitable host system as developed and practiced by the ordinary artisan. The macromolecule can also be composed of both protein and nucleic acid, and may be formed in a crystallization drop chamber (described below) by mixing a protein solution with a nucleic acid solution, wherein the nucleic acid is a substrate for the protein, and the two can contact each other to form a protein-nucleic acid complex that may then be capable of binding to a ligand. In this case, the protein-nucleic acid complex represents a "target" or a "macromolecule" that can putatively bind to a ligand. Preferred macromolecules are any protein, nucleic acid or protein-nucleic acid complex where it is known that ligand binding to the macromolecule causes a conformational change in the macromolecule. Specific examples of such macromolecules include but are not limited to kinases, proteases [Bernstein et al.], phosphatases [Scapin et al., Jia et al.], and nucleic acid polymerases [Huang et al.]. Macromolecules can also include receptors, such as nuclear hormone receptors, and generally extracellular receptors of signaling molecules.

In a first embodiment, this invention relates to a ligand screening method referred to as the "crystal growth dependence on ligand" assay (shortened to "crystal growth assay") and comprises providing a solution containing a macromolecule and exposing the solution to a potential ligand. Solution conditions are optimized such that the macromolecule does not crystallize in the absence of binding ligand and only forms crystals in the presence of binding ligand. Therefore, formation of crystals when the macromolecule solution is exposed to one or more potential ligands indicates that at least one ligand has bound to the macromolecule.

In the crystal growth assay of the invention, a preferred technique for optimizing co-crystallization conditions is to provide the macromolecule and ligand in separate macromolecule and ligand solutions and to identify a solution that promotes the formation of macromolecule/ligand co-crystals when macromolecule and ligand are both present, but does not promote the formation of apo-crystals when only the macromolecule is present and the ligand is absent, is identified. The solution identified is referred to as a co-crystallization promoting solution.

Storage solutions for proteins and nucleic acids and other macromolecules are well known in the art and typically comprise water as a solvent and a buffering acid-base conjugate pair to maintain pH. It is typically desirable to include protein stabilizing agents in the storage solution which may include buffers, reducing agents, glycerol, detergents, polyols, metal chelating agents, salts, cofactors, substrates, and metal ions.

Ligand storage solutions are also well known in the art. Often ligands are hydrophobic in nature and do not readily dissolve in water. Therefore, it is typically desirable to dissolve the ligand in an organic solvent such as a polar protic or aprotic solvent. Examples of suitable solvents include ethanol, acetone or DMSO. The organic solutions are often diluted with water until the ligand reaches its solubility point. This produces co-solvent (organic—water) solutions containing dissolved ligand.

The co-crystallization promoting solution can differ from either the protein storage solution or ligand storage solution in several different ways, such as, but not limited, the following features: concentration of protein, concentration of ligand, concentration and nature of pH maintaining reagents, concentration and nature of stabilizers, concentration and nature of salts, concentration and nature of metal ions, concentration and nature of polyols, or concentration and nature of any chemicals that can be dissolved into the solution. Co-crystallization promoting solutions are well known in the art.

One example of a technique for identifying a co-crystallization promoting solution that promotes the formation of macromolecule/ligand co-crystals when macromolecule and ligand are both present, but does not promote the formation of apo-crystals when only the macromolecule is present is as follows. Macromolecule storage solution with or without dissolved macromolecule is mixed with ligand storage solution with or without dissolved ligand, and these mixtures are then further modified by the addition of a co-crystallization promoting solution. These final mixtures are then further modified by vapor diffusion means due to solvent transfer by vapor diffusion from a "reservoir" of co-crystallization promoting solution, and a separate "drop chamber" containing the final mixture.

This technique is a vapor diffusion technique and involves the use of a physically closed system comprised of a reservoir chamber containing the potential co-crystallization promoting solution, and a drop chamber containing aforementioned mixture. Such techniques are described in U.S. Pat. Nos. 6,267,935 and 6,039,804, each of which is herein incorporated by reference in its entirety. As will be apparent to those in the art, the reservoir chamber is physically positioned with respect to the drop chamber so as to allow vapor diffusion to occur. Vapor diffusion techniques are well known in the prior art, and include, for instance, the sitting drop method [Carter et al.], the sandwich drop method, and the hanging drop method. For example, in the sitting drop method, a co-crystallization solution is placed into the reservoir chamber, and a smaller volume of the same solution is placed into an adjacent drop chamber. This is followed by mixing of a ligand solution into the co-crystallization solution in the adjacent drop chamber. In turn, this is followed by mixing of a protein solution, into the drop chamber. The reservoir and drop chambers are sealed with clear tape, and the crystallization plate is stored in a temperature controlled environment, which can be between about 0° C. and 35° C., preferably between about 10° C. to 20° C., more preferably at about 16° C. Exposure of the drop chamber solution mixture to the reservoir solution through the vapor phase results in vapor diffusion of solvent into or out of the solutions in either chamber depending on their relative vapor pressure osmolalities. This diffusion modifies both solutions.

In a preferred technique for evaluating co-crystallization promoting solutions, four individual drop chambers, each connected to a common reservoir via dedicated vapor diffusion channels [Kim et al., U.S. Pat. No. 6,039,804], are configured with four different combinations of solutions as follows:

a. protein solution, plus ligand solution, plus co-crystallization solution b. protein storage solution without any dissolved protein, plus ligand solution, plus co-crystallization solution.

c. protein solution, plus ligand storage solution without any dissolved ligand, plus co-crystallization solution.

d. protein storage solution without any dissolved protein, plus ligand storage solution without any dissolved ligand, plus co-crystallization solution.

It will be recognized by those trained in the art, that each of these four experimental configurations can be set up as individual drop chambers in vapor diffusive communication with a single dedicated reservoir. It will also be recognized by those trained in the art that a plurality of co-crystallization solutions can be used [Hol et al.]. Such a plurality of co-crystallization solutions could be similar or identical to the solution examples listed in TABLE 1.

The solutions present in the drop chambers are visually inspected over time to identify the co-crystallization solutions which promote crystal formation only when protein and ligand are both present in the drop chamber. It will be recognized by those trained in the art that it is possible to obtain crystals in drop chambers that contain only protein or only ligand, and that such crystals may be of a different morphology or space group compared to crystals that might grow when both protein and ligand are present together. It will also be recognized by those trained in the art that it may be possible to obtain salt crystals in any of the drop chambers. Such salt crystals would be comprised of one or more chemical component of the drop chamber solutions, but not protein or ligand.

Once lead macromolecule-ligand co-crystallization solutions have been evaluated, these leads can be optimized in a variety of ways. One example of this optimization procedure typically involves varying the crystallization solution chemical composition and volume, as well as the concentration of macromolecule and ligand volumes and concentrations that go into the crystallization drop mixture. For example, chemical components of the putative co-crystallization solution(s) can be varied systematically in concentration to produce a fine grid screening set of multiple new co-crystallization solutions that have slightly varied composition that closely approximates one or more of the individual putative co-crystallization solutions. Components that are typically varied include precipitant (type and concentration), salt (type and concentration), and buffer (type, concentration and pH). Another optimization strategy is to produce a set of crystallization solutions that are prepared from all possible combinations of chemical components that exist in each of the lead putative co-crystallization solutions. See Example 5 below for an illustration of this approach called the "CBS-Cross" optimization strategy. The optimization sets of crystallization solutions are used to screen for co-crystallization of macromolecule and ligand under the following four different combinations of solutions in crystallization drop chambers as follows:

a. macromolecule solution, plus ligand solution, plus putative co-crystallization solution b. macromolecule storage solution without any dissolved macromolecule, plus ligand solution, plus putative co-crystallization solution.

c. macromolecule solution, plus ligand storage solution without any dissolved ligand, plus putative co-crystallization solution.

d. macromolecule storage solution without any dissolved macromolecule, plus ligand storage solution without any dissolved ligand, plus putative co-crystallization solution.

The solutions present in the drop chambers that are prepared are visually inspected over time to determine which of the co-crystallization solutions provide the largest and most well formed macromolecule-ligand co-crystals which would be identified as such since they would only be present in the crystallization drops that contained both the macromolecule and ligand, but not present in any drops where either macromolecule or ligand were not included. In this way, an optimized co-crystallization promoting solution can be identified based on its optimized ability to promote the formation of macromolecule-ligand co-crystals. Confirmation that optimized macromolecule-ligand co-crystals are comprised of macromolecule-ligand complexes can then be provided by solving the structure of the crystals by X-ray diffraction methods.

Once a co-crystallization promoting solution is identified for a certain macromolecule, ligands can be evaluated for their ability to bind to the macromolecule based on their ability to form crystals with the macromolecule under crystallization conditions identified to promote the growth of macromolecule-ligand co-crystals, but not promote the formation of apo-macromolecule crystals. According to the preferred embodiment of this step of the method, macromolecule-ligand co-crystallization experiments are conducted under defined conditions with crystallization drops that contain volumes of co-crystallization promoting solution, macromolecule solution, and ligand solution that are known to yield only macromolecule-ligand co-crystals if the ligand is capable of binding to the macromolecule. The ligands used are not necessarily known to bind to the macromolecule. As such, if a ligand is found to promote crystal growth under these conditions, then this is taken as evidence that the ligand in question is capable of binding to the macromolecule and promoting a conformation of the macromolecule such that the resulting macromolecule-ligand complex is capable of crystallizing under the defined conditions. Confirmation that the resulting macromolecule-ligand co-crystals are comprised of macromolecule-ligand complexes is optionally provided by solving the structure of the crystals by X-ray diffraction methods. If a ligand is found to be unable to promote crystal growth under these conditions, then this information is taken as evidence that the ligand in question either does not bind to the macromolecule, or if binding to the macromolecule does occur then the ligand binding mode is such that it does not promote crystal formation under the defined conditions.

The assay can also be carried out with multiple potential ligands simultaneously, as described for the single potential ligand. Again, observation of crystals identifies that at least one of the potential ligands binds to the macromolecule. The binding ligand can then be identified by techniques well known in the art. For example, the assay can be rerun individually with each potential ligand in order to identify which of the ligands is the binding ligand.

In a second embodiment, the invention relates to a screening method that comprises providing a crystal of a macromolecule and exposing the crystal to one or more potential ligands. Cracking of the crystal after exposure to the potential ligand(s) indicates binding between at least one potential ligand and the macromolecule. This assay is referred to herein as the "crystal-cracking" assay.

The crystal cracking assay of the invention involves the development of optimized crystal growth conditions that depend on the absence of the ligand to produce a supply of macromolecule crystals, referred to herein as apo-crystals, then soaking the apo-crystals in a solution containing one or more potential ligands. If a ligand actually binds to the macromolecule, it initiates a conformational change in the crystal resulting in an observable cracking of the crystal.

Macromolecules can be crystallized in the absence of ligand by published conditions or by other methods well established in the art. One method of obtaining apo-crystals of macromolecules, for example where the macromolecule is a protein, is as follows.

The protein is dissolved in a solution to form a protein solution. This step may be achieved by a number of methods. For example, the protein may be prepared from cell lysates by liquid column chromatography followed by collection of the pure protein fractions, pooling the fractions and then dialyzing them into the appropriate final protein storage solution using the appropriate molecular weight cut off dialysis material. Alternatively, a protein may be directly dissolved in the protein storage solution. Other alternatives for preparing the protein dissolved in the protein storage solution would be to subject a dissolved protein solution to gel filtration (size exclusion chromatography), ultrafiltration, or centrifugal filtration to exchange the existing protein storage solution for an alternative protein storage solution. It is typically desirable to include protein stabilizing agents in the protein storage solution which may include buffers, reducing agents, glycerol, detergents, polyols, metal chelating agents, salts, cofactors, substrates, and metal ions.

The one or more potential ligands to which the apo-crystal is exposed are preferably provided in a solution. The solvent of the ligand solution should not by itself cause cracking of the macromolecule crystal. Dissolution or dispersion of a potential ligand in a solution, to form a ligand solution, can be achieved by a number of methods well known in the art. For example, the ligand may be directly dissolved in ligand storage buffer. Alternatively, a ligand may be prepared from synthetic reactions and purified by liquid column chromatography followed by collection of pure ligand fractions, pooling the fractions and drying down the fractions under vacuum. Often ligands are hydrophobic in nature and do not readily dissolve in water. Therefore, it is typically desirable to dissolve the ligand in an organic solvent such as ethanol or DMSO. The organic solutions are often diluted with water until the ligand reaches its solubility point. This produces co-solvent (organic—water) solutions containing dissolved ligand.

Solutions that promote crystal growth only in the absence of ligand, referred to herein as "apo-macromolecule crystallization promoting solutions," can be identified, for example, by the same procedure described above for co-crystallization promoting solutions. This procedure is modified so that the crystallization drops are examined to identify crystallization promoting solutions that produced crystals only when macromolecule is present and ligand is absent.

Once lead apo-macromolecule crystallization solutions have been evaluated, these leads are optimized as discussed above for the optimization of the co-crystallization promoting solutions, except that apo-macromolecule crystallization solutions and experimental crystallization drop set ups are optimized for their effectiveness at producing the largest and most well formed apo-macromolecule crystals which are identified as such since they are only present in the crystallization drops that contain the macromolecule and no ligand, and not present in any drops where both macromolecule or ligand were included. Confirmation that optimized apo-macromolecule crystals are comprised of apo-macromolecules can then be optionally provided by solving the structure of the crystals by X-ray diffraction methods.

Identification of a ligand of the macromolecule is conducted by soaking the apo-crystal of the macromolecule in a suitable crystal soaking solution, which is a solution that does not itself promote cracking of the crystal in the absence of ligand. An example of a technique for identifying a suitable crystal soaking solution is as follows. A small volume, typically 0.1 to 1 microliter, of ligand solution (described above) that does not contain any dissolved ligand, is added to a crystallization drop that contains apo-macromolecule crystals. The new solution that then comprises the crystallization drop (representing the apo-macromolecule crystallization solution and the "macromolecule solution" that were originally placed into the drop, plus changes in drop volume due to vapor diffusion, plus the crystal soaking solution that was added to the drop) represents a putative "crystal soaking solution." The apo-macromolecule crystals that are present in the crystallization drop are monitored visually for a several hours to days to determine if any crystal deterioration is observed. This can be done through standard light microscopy or examination of the X-ray diffraction properties of the treated crystals relative to untreated crystals.

Another example of a technique for identifying a suitable crystal soaking solution is as follows. Apo-macromolecule crystals are transferred from their crystallization drop in a small volume of the crystallization drop solution into a much larger volume of potential crystal soaking solution, which in this case may typically be composed of a mixture of the apo-macromolecule crystallization promoting solution and a ligand solution that does not contain any ligand. The apo-macromolecule crystals are then monitored visually for several hours to days to determine if any crystal deterioration is observed. In this way, suitable "crystal soaking solutions" can be identified which, in the absence of ligand, will maintain the apo-macromolecule crystals with out significant deterioration.

Although not required, it is preferred that the ability of apo-macromolecule crystals to crack upon being soaked in a suitable crystal soaking solution which contains a dissolved ligand which is known to bind to the macromolecule is evaluated. This procedure provides a positive control for examining the ability of other ligands to bind to the macromolecule by virtue of their ability or inability to promote crystal cracking or deterioration.

Thus, for example, a pre-determined small volume, typically 0.1 to 1 microliter, of ligand solution is added to a crystallization drop that contains apo-macromolecule crystals. Preferably, the mole ratio of ligand to macromolecule is at least about 0.1 moles of ligand to about 1 mole of macromolecule. The apo-macromolecule crystals that are present in the crystallization drop are monitored visually for a several hours to days to determine if any crystal cracking or deterioration is observed. This monitoring or observation can be done through visual observation, by magnifying glass, or microscope, or by standard light microscopy or by examination of the X-ray diffraction properties of the treated crystals relative to untreated crystals. The volume of ligand solution added to the crystallization drop will have previously been shown to produce a suitable crystal soaking solution when added, without any dissolved ligand, to apo-macromolecule crystallization drops of similar volume.

Alternatively, as another example, the evaluation of the ability of the apo-crystals to crack when exposed to a known ligand can involve physical transfer of apo-macromolecule crystals from their crystallization drop in a small volume of the crystallization drop solution into a much larger volume of a known crystal soaking solution that contains a dissolved ligand that is known to bind to the macromolecule. The apo-macromolecule crystals are then monitored visually for several hours to days to determine if any crystal cracking or deterioration is observed. If crystal cracking or deterioration is observed when a known ligand is present in the crystal soaking solution then this procedure provides a positive control for examining the ability of other ligands to bind to the macromolecule by virtue of their ability or inability to promote crystal cracking or deterioration.

The next step of this embodiment of the invention is the evaluation of the ability of potential ligands for binding to a macromolecule based on their ability to promote cracking of apo-macromolecule crystals when the apo-crystals are placed into a suitable crystal soaking solution containing the dissolved ligand(s), and wherein it is already known that soaking the apo-macromolecule crystals with the same crystal soaking solution containing a known macromolecule-binding ligand will result in the cracking of the apo-macromolecule crystals as previously determined in with the control experiment above. This step of the method is similar to the procedure used to provide a positive control, except that the ligands used are not necessarily known to bind to the macromolecule that forms the apo-macromolecule crystals. Preferably, the mole ratio of ligand to macromolecule used is at least about 0.1 moles of ligand to about 1 mole of macromolecule. If crystal cracking or deterioration is observed when a new ligand is present in the "crystal soaking solution" then this is taken as evidence that the ligand in question can bind to the macromolecule. If no crystal cracking or deterioration is observed then this is taken as evidence that the new ligand does not bind to the macromolecule, or if binding to the macromolecule does occur then the ligand binding mode is such that it does not promote crystal deterioration. Again, crystal cracking can be observed or monitored by a variety of techniques including by visual inspection with the naked eye, a magnifying glass, or microscope, or by standard light microscopy or by examination of the X-ray diffraction properties of the treated crystals relative to untreated crystals.

If more than one ligand is present in the solution, crystal cracking reveals that at least one of the ligands in the solution has bound to the macromolecule. The ligand or ligands which have bound to the macromolecule can then be identified by methods well known in the art. For example, the assay can be rerun individually with each potential ligand in order to identify which of the ligands is the binding ligand.

The following examples are illustrative of various aspects of the invention but do not serve to limit its scope.

EXAMPLES

Some abbreviations used herein are as follows:
MES—[2-(N-morpholino)ethanesulfonic acid]
HEPES—N-2-hydroxyethylpiperazine-N-2
TRIS—[tris-(hydroxymethyl)-aminomethane]
DMSO—dimethyl sulfoxide
CHAPS—3 [(3-cholamidopropyl) dimethylammonio]-1-propanesulfonate
BOG—n-hexyl-b-D-glucopyranside
ACES—(N-2-acetamido-2-aminoethane-sulfonic acid)
BES—[N,N-bis-(2-hydroxyethyl)-2
Bicine—[N,N-bis-(2-hydroxyethyl)-glycine]
BIS-Tris—{[bis-(2-hydroxyethyl)-imino]-tris-(hydroxymethyl)-methane}
BIS-Tris-propane—{1,3-bis-[tris-(hydroxylmethyl)-methylamino]-propane}
CAPS—[3-(cyclohexylamino)-propane-sulfonic acid]
CHES—[2-(N-cyclohexylamino) ethanesulfonic acid]
HEPES—(N-2-hydroxyethylpiperazine-N'-2-ethanesulfonic acid)
MOPS—[3-(N-morpholino) propanesulfonic acid]
PIPES—[piperazine-N,N'-bis-)2-ethanesulfonic acid]
TAPS—(3-{[tris-(hydroxymethyl)-methyl]-amino}-propanesulfonic acid)
TES—(2-{[tris-(hydroxymethyl)-methyl]-amino}-ethanesulfonic acid)
Tricine—{N-[tris-(hydroxylmethyl-methyl]-glycine}.

The following examples of how to obtain apo-protein crystals and protein-ligand co-crystals involve the use of recombinant form of human DNA topoisomerase I ("topo I") and 22 base pair duplex DNA substrates which permanently trap topo I in a covalent topo I-DNA complex. This enzyme-DNA complex is one example of a "protein-substrate complex."

Topoisomerase I (Topo I) is an essential eukaryotic enzyme that acts to relax torsional stress in supercoiled DNA generated during transcription and replication [Champoux et al.]. Topo I mediates DNA relaxation by creating a transient single strand break, allowing the broken strand to rotate around its intact complement. This nicking results from the transesterification of an active-site tyrosine at a DNA phosphodiester bond forming a 3'-phosphotyrosine covalent enzyme-DNA complex. After DNA relaxation, the covalent intermediate is reversed when the released 5'-OH of the broken strand re-attacks the phosphotyrosine intermediate in a second transesterification reaction [Champoux et al.].

Topo I is the sole molecular target of a family of anticancer compounds called camptothecins [Wall et al., Nitiss et al., Hsiang et al.] (CPTs). It is generally believed that CPTs act as uncompetitive inhibitors by binding to the covalent Topo I-DNA intermediate and blocking the second transesterification reaction [Hertzberg et al.], thus converting the enzyme into a molecular poison [Chen et al.].

Camptothecin and its derivatives are known to interact with topo I only when it is in covalent complex with DNA (after having cleaved one strand of the duplex). Under normal circumstances, the cleavage event is highly transitory and is rapidly reversed by a ligation event.

EXAMPLE 1

Preparation of Topoisomerase I Construct

The 70 kDa human topoisomerase I construct of residues Lys175 to Phe765 (topo70, missing the non-essential unconserved NH2-terminal domain) was purified from a baculovirus-insect cell (SF9) expression system [Stewart et al., J. Biol. Chem, 1996, 271, 7593]. Final preparations of topo70 were concentrated to 3 or 4 mg/ml in 10 mM Tris-HCl pH 7.5, 1 mM EDTA, and 1 mM DTT.

EXAMPLE 2

Trapping of Topo-I DNA Complex

Crystallographic studies required that the transient covalent topo I-DNA complex be trapped with the aid of a "suicide substrate" which is composed of a high affinity DNA binding site that contains a 5'-bridging phosphorothiolate at the point of topo I cleavage. Breakage at a 5'-bridging phosphorothiolate results in permanent trapping of the covalent complex since the resulting 5'-terminal sulfhydryl group on the broken strand is not a sufficient nucleophile to promote religation [Burgin et al.].

Blunt ended duplex oligonucleotides were prepared with a 5'-bridging phosphorothiolate linkage at the preferred site of topo I cleavage on the cleaved strand of the duplex [Burgin et al., Redinbo et al.]. The cleaved strand was prepared by first synthesizing protected 5'trityl-S-2',5'-dideoxyribonucleoside-3'-O-phosphoramidite building blocks that were then used in standard phosphoramidite oligonucleotide synthesis procedures to produce oligonucleotide material with a 5' bridging phosphorothiolate bond at the site of topo I cleavage. The cleaved strand had the sequence 5'-AAAAAGACTTsTGAAAAATTTTT-3', [SEQ ID NO:1], where "s" represents the 5' bridging phosphorothiolate linkage. This strand was annealed to a complementary strand of the sequence 3'-TTTTTCTGAAACTTTTTAAAAA-5' [SEQ ID NO:2] to form a duplex suicide oligonucleotide substrate. This was achieved by mixing purified oligonucleotides dissolved in water at a 1:1 molar ratio of cleaved to complementary strand such that the concentration of each strand was at least 0.1 mM. The oligonucleotide mixture was adjusted to 6 mM NaCl with the addition of the appropriate volume of 500 mM NaCl. This oligonucleotide mixture was then heated to 80° C. and allowed to cool slowly to room temperature over 8 hours, to produce the annealed duplex oligonucleotide substrate. The final annealed duplex solution was adjusted with the addition of water and/or 500 mM NaCl such that the final concentration of NaCl was 6 mM and the oligonucleotide duplex was either 0.1 mM or 0.05 mM as defined more precisely in each case described below.

EXAMPLE 3

Crystallization Trials

Initial crystallization trials with topo70 and the suicide duplex DNA substrate were conducted in sitting drop format using a Cryschem sitting drop crystallization tray [Carter et al.] (marketed by Charles Supper, Inc). The crystallization screening solutions used were the first 48 solutions from the Crystal Screen Kit [see Hampton Research Solutions for Crystal Growth] (marketed by Hampton Research, Inc.), the 48 solutions from the Wizard I Crystal Growth Matrix [Hol et al.] (marketed by Emerald BioStructures, Inc., see also Table I), and the 48 solutions from the Wizard II Crystal Growth Matrix [Hol et al.] (marketed by Emerald BioStructures, Inc., see also Table 2). The crystallization experiments were set up by first placing 500 microliters of each of the crystallization screening formulations into the reservoir chambers of Cryschem crystallization trays. Each tray has 24 reservoir chambers. Therefore, 6 trays were required to screen all 144 crystallization screening formulations representing 1 to 48 of Crystal Screen Kit, 1 to 48 of Wizard I Crystal Growth Matrix, and 1 to 48 of the Wizard I Crystal Growth Matrix. Once the crystallization solutions had been individually placed into the reservoir chambers, 3 microliters of each individual crystallization screening formulation was placed into the sitting drop chamber located within the reservoir chamber. This was followed by the addition of 1 microliter of duplex suicide oligonucleotide substrate (0.1 mM duplex, 6 mM NaCl) into the drop chamber. The duplex was mixed with the crystallization screening solution by repeated pipetting. This was followed by the addition of 2 microliters of purified topo70 at 3 mg/ml in 10 mM Tris-HCl pH 7.5, 1 mM EDTA, and 1 mM DTT. The Cryschem trays were sealed with crystal clear sealing tape (marketed by Manco, Inc. Avon, Ohio), and incubated at 16° C. The drop chambers of the crystallization trays were visually observed two days following set up, and putative topo70-DNA enzyme-substrate crystals were found to have grown in the crystallization drops that contained Crystal Screen formulation #36 ( 8% w/v PEG 8000, 100 mM Tris-HCl pH 8.5 ), Wizard I formulation #32 (10% w/v PEG 3000, 100 mM Na/K phosphate pH 6.2), Wizard II formulation #8 (10% w/v PEG 8000, 100 mM Na/K phosphate pH 6.2, 100 mM NaCl), and Wizard II formulation #22 (10% v/v 2-propanol, 100 mM imidazole pH 8.0).

These initial screening results were used to prepare four new crystallization screening solutions which were given the designation "VII-2" which stands for the second "2" crystallization screen to obtain the seventh "VII" crystal form of human topo I (Form 7, the topo70-DNA covalent complex crystal form discussed below). The four different VII-2 formulations each contained one or more of the chemical components found in the lead crystallization conditions, plus additional components such as 10 mM DTT. The four VII-2 crystallization conditions were as follows:

VII-2 #1. 10% v/v 2-propanol, 100 mM imidazole pH 8.0, 10 mM DTT

VII-2 #2. 8% w/v PEG 8000, 100 mM Tris-HCl pH 8.5, 10 mM DTT

VII-2 #3. 10% w/v PEG 8000, 100 mM Tris-HCl pH 8.5, 10 mM DTT

VII-3 #4. 10% w/v PEG 3000, 100 mM Na/K phosphate pH 6.2, 100 mM MES pH 6.6, 10 mM DTT.

A Cryschem tray was used to screen each of the four VII-2 crystallization solutions for their ability to promote crystallization of topo70-DNA complexes in the absence or presence of Topotecan, an analogue of camptothecin. The crystallization experiments were set up by first placing 500 microliters of the VII-2 screening solutions in duplicate individual reservoir chambers. Next, 3 microliters of each reservoir solution was placed into the drop chambers. The drop chamber solutions were then mixed by pipetting with 1.5 microliters of 0.05 mM suicide duplex oligonuceotide substrate in 6 mM NaCl. One microliter of 1 mM Topotecan in pure water or 1 microliter of pure water only was added to each of the duplicate drop chambers. Then 2 microliters of topo70 at 3 mg/ml in 10 mM Tris-HCl pH 7.5, 1 mM EDTA, and 1 mM DTT was added to each of the drop chambers. The crystallization tray was sealed with crystal clear sealing tape (marketed by Manco, Inc. Avon, Ohio), and incubated at 16° C. The drop chambers of the crystallization tray was visually observed several days following set up, and putative topo70-DNA covalent complex crystals were found to grow in condition VII-2 #3 only when Topotecan was absent.

Several rounds of similar optimization screening experiments eventually led to the identification of a definitive crystallization condition that produces crystals of the topo70-DNA covalent complex only in the absence of Topotecan (designate Form 7). The Form 7 crystals were grown at 16° C. under optimized conditions by vapor diffusion equilibration against a 500 microliter reservoir solution of 10% PEG 8000, 100 mM Tris-HCl pH 8.0, 100 mM Na/K phosphate pH 6.2, 100 mM KCl, and 10 mM DTT. The sitting drop crystallizations were prepared in drop chambers by mixing 2 microliters of reservoir solution with 2 microliters of 0.1 mM duplex DNA substrate in 6 mM NaCl, and 2 microliters 4 mg/ml topo70 in 10 mM Tris-HCl pH 7.5, 1 mM EDTA, and 1 mM DTT.

The structure determination of the Form 7 crystals revealed that they are comprised of the expected topo70-DNA covalent complex (the topo70 protein in covalent complex with the 22mer duplex DNA). For structure determination and refinement, Form 7 crystals were cryoprotected by soaking them in plus 30% v/v PEG 400, 100 mM Tris-HCl pH 8.0, 100 mM Na/K phosphate pH 6.2, 100 mM KCl, 10 mM DTT, for 30 seconds followed by flash freezing in liquid nitrogen. X-ray diffraction data were collected at 100 K at the National Synchrotron Light Source (NSLS), Brookhaven National Laboratory beamline X25, and COM-CAT, Sector 32 of the Advanced Photon Source, Argonne National Laboratory. The structures were solved by molecular replacement with AMORE [Navaza] by using the previously determined structure of the non-covalent topo70-DNA complex [Stewart et al. Science 1998, 279, 1534]. The DNAs were placed into the electron density of sigma-a weighted phase-combined maps and rigid body refined using CNX. The models were rebuilt and refined by CNX with torsion angle simulated annealing [Brunger et al.], restrained B-factor refinement, and iterative model adjustments with XtalView [McRee]. For Form7 crystals, merohedral twinning was detected and the twin fraction estimated using CNX. The binary model was refined using torsion angle simulated annealing and restrained B-factor refinement against the twinned data using CNX.

EXAMPLE 4

Crystal Cracking of Form 7 Crystals

In order to test the effects of Topotecan and other topo I poisons on the integrity of Form 7 crystals, crystallization drops containing Form 7 crystals were subjected to the following treatments:

1. Injection of 3 microliters of a buffer solution containing 100 mM MES pH 6.3, and 100 mM Na/K phosphate pH 6.2 (buffer only control).

2. Injection of 3 microliters of 100 mM MES pH 6.3, 100 mM Na/K phosphate pH 6.2, and 0.32 mM Topotecan.

3. Injection of 3 microliters of 100 mM MES pH 6.3, 100 mM Na/K phosphate pH 6.2, 13% v/v DMSO, and 0.64 mM camptothecin.

4. Injection of 3 microliters of 100 mM MES pH 6.3, 100 mM Na/K phosphate pH 6.2, 13% v/v DMSO, and 0.64 mM 10,11 MDO camptothecin.

After incubating the treated crystallization drops at 16° C. for approximately 3 hours, it was observed that Form 7 crystals treated under condition #1 (buffer only control) showed no visible signs of deformity. They appeared to be unaffected by the treatment. In contrast, the crystals treated with Topotecan and camptothecin under conditions #2 and #3 showed visible signs of micro cracks throughout the crystals. The crystals treated with 10,11 MDO-camptothecin had dissolved leaving only a trace pile of crystal bits where previously there were crystals. These results demonstrate that Form 7 apo-crystals (topo70-DNA covalent complex crystals) will undergo cracking when soaked with topotecan or other camptothecin derivatives [Stewart et al. Drug Discovery Today 2002, 7, 187–196]. Moreover, the Form 7 crystals will not grow in the presence of topotecan.

EXAMPLE 5

Crystal Growth Assay

A combinatorial "Crystallant, Buffer, Salt" (CBS-cross) crystallization screening approach was employed to identify crystallization conditions of the topo70-DNA covalent complex wherein crystal growth depends on the presence of Topotecan (a highly water soluble derivative of CPT). The CBS-cross method started with a list of all known lead crystallization conditions for topo70 as well as the reconstituted form of human topo I called topo58/6.3 [Stewart et al, 1997; Redinbo et al., 1998; Stewart et al., 1998] in non-covalent and covalent complex with DNA. The chemical components of each crystallization formulation were classified as being either a crystallant, buffer, or salt. The various crystallants were as follows:

1. 30% v/v PEG 400 (PEG 400 is polyethylene glycol Mwt. 400, CAS# 25322-68-3, and is available from Fluka catalogue #81170).

2. 20% w/v PEG 1000 (PEG 1000 is polyethylene glycol Mwt. 1000, CAS# 25322-68-3, and is available from Fluka catalogue #81189).

3. 20% w/v PEG 3000 (PEG 3000 is polyethylene glycol Mwt. 3000, CAS# 25322-68-3, and is available from Fluka catalogue #81227).

4. 20% w/v PEG 2000 MME (PEG 2000 MME is polyethylene glycol monomethyl ether, Mwt. 2000, CAS#9004-74-4, and is available from Fluka catalogue #81321).

5. 10% w/v PEG 8000 (PEG 8000 is polyethylene glycol Mwt. 8000, CAS# 25322-68-3, and is available from Fluka catalogue #81268).

The various buffers were composed of a conjugate acid-base pair as follows:

1. 100 mM Citrate/citric acid pH 5.5
2. 100 mM Na2 H /K H2 phosphate pH 6.2
3. 100 mM MES/NaOH pH 6.4
4. 100 mM ADA/NaOH pH 6.5
5. 100 mM Tris/HCl pH 7.0
6. 100 mM Tris/HCl pH 8.5

The various salts were as follows:

1. 200 mM NaCl
2. 200 mM Li2SO4
3. 200 mM KCl
4. 200 mM Na2 H /K H2 phosphate pH 6.2 (a buffer considered to be a salt in this case).

CBS-cross crystallization screening formulations were prepared with all possible combinations of crystallants, buffers and salts. For example the 24 possible CBS-cross crystallization solutions that contain 10% w/v PEG 8000 have been given the designation "T80P" as shown in Table 3.

In one set of crystallization experiments, the T80P crystallization screen was used in a Combinatorial Clover Plate developed by Emerald BioStructures, Inc. [Kim et al.], which allows for the rapid set up of multiple crystallizations in a common vapor diffusive environment.

The 24 reservoir chambers of the Combinatorial Clover Plate were filled with 1.0 milliliter of each of the 24 different T80P formulations. Once the T80P formulations had been individually placed into the reservoir chambers, 2 microliters of each individual crystallization screening formulation was placed into each of the four the sitting drop chambers that are connected to the common reservoir by dedicated vapor diffusion channels. This was followed by the addition of 1 microliter of duplex suicide oligonucleotide substrate (0.05 mM duplex, 6 mM NaCl) into the drop chamber. The cleaved strand of the duplex had the sequence 5'-AAAAAGACTTsGGAAAAATTTTT-3' [SEQ ID NO:1], where "s" represents the 5' bridging phosphorothiolate linkage. This strand was annealed to a complementary strand of the sequence 3 '-TTTTTCTGAACCTTTTTAAAAA-5' [SEQ ID NO:2] to form a duplex suicide oligonucleotide substrate as described in Example #2.

The duplex was mixed with the crystallization screening solution by repeated pipetting. This was followed by the addition 0.1 microliter of 10 mM Topotecan to the upper two drop chambers of each crystallization clover. The lower two drop chambers did not receive any Topotecan. The left two drop chambers of each crystallization clover then received 1 microliter of purified topo70 at 4 mg/ml in 10 mM Tris-HCl pH 7.5, 1 mM EDTA, and 1 mM DTT. The right two drop chambers of each crystallization clover then received 1 microliter of purified mutant N722S topo70 (containing an Asn722Ser point mutation) at 4 mg/ml in 10 mM Tris-HCl pH 7.5, 1 mM EDTA, and 1 mM DTT. The Combinatorial Clover Plate was sealed with crystal clear sealing tape (marketed by Manco, Inc. Avon, Ohio), and incubated at 16° C. The drop chambers of the crystallization trays were visually observed 7 and 28 days following set up.

With this experimental design, the four drop chambers of each crystallization clover received the following components:

Upper Right Drop Chamber: 1 microliter T80P formulation, 1 microliter of 0.05 mM suicide duplex DNA substrate, 0.1 microliter of 10 mM Topotecan, and 1 microliter of 4 mg/ml N722S Topo70.

Upper Left Drop Chamber: 1 microliter T80P formulation, 1 microliter of 0.05 mM suicide duplex DNA substrate, 0.1 microliter of 10 mM Topotecan, and 1 microliter of 4 mg/ml Topo70.

Lower Right Drop Chamber: 1 microliter T80P formulation, 1 microliter of 0.05 mM suicide duplex DNA substrate, and 1 microliter of 4 mg/ml N722S Topo70.

Lower Left Drop Chamber: 1 microliter T80P formulation, 1 microliter of 0.05 mM suicide duplex DNA substrate, and 1 microliter of 4 mg/ml Topo70.

Since the four different crystallization drop chambers are exposed to the same reservoir solution by vapor diffusion, any observed differences in crystallization will result from differences in the types of components present in the drop chamber, rather than by experimental error that could result from having to set up multiple individual crystallization experiments exposed to individual reservoir solutions.

On day 28 it was observed that the crystallizations conducted with T80P #9 and T80P #10 crystallization formulations produced crystals of distinct block morphology when Topotecan was present in the drop chamber but not when Topotecan was absent. These conditions were optimized further by varying the volumes of components that were added to the crystallization drop. Specifically, it was found that larger drop volumes produced larger crystals. The optimal crystallization condition was found to be achieved with T80P #9 (10% w/v PEG 8000, 100 mM MES/NaOH pH 6.4, 200 mM Li2SO4) wherein each drop chamber received 2 microliters of T80P#9, 1.5 microliter of 0.05 mM suicide duplex substrate, 0.1 microliter of 10 mM Topotecan, and 1.5 microliter of purified topo70 at 4 mg/ml in 10 mM Tris-HCl pH 7.5, 1 mM EDTA, and 1 mM DTT. Incubation at 16° C. produced crystals (designated "Form 9" crystals).

The structure determination of the Form 9 crystals have revealed that they are comprised of the expected Topo70-DNA covalent complex with Topotecan bound (the Topo70 protein in covalent complex with the 22mer duplex DNA, with bound Topotecan).

For structure determination and refinement, Form 9 crystals were cryo-protected by soaking them in 30% v/v PEG 400, 100 mM MES/NaOH pH 6.4, 200 mM Li2SO4, 1 mM Topotecan, for 30 seconds followed by flash freezing in liquid nitrogen. X-ray diffraction data were collected at 100K at the National Synchrotron Light Source (NSLS), Brookhaven National Laboratory beamline X25, and COMCAT, Sector 32 of the Advanced Photon Source, Argonne National Laboratory. The structures were solved by molecular replacement with AMORE [Navaza et al.] by using the previously determined structure of the non-covalent Topo70-DNA complex [Stewart et al., 1998]. The DNAs were placed into the electron density of sigma-a weighted phase-combined maps and rigid body refined using CNX. The models were rebuilt and refined by CNX with torsion angle simulated annealing [Brunger et al.], restrained B-factor refinement, and iterative model adjustments with XtalView [McRee].

Topotecan was placed unambiguously into the sigma-a weighted |Fobs|-|Fcalc| maps. The final complex model contains residues 201 to 765 of Topo70, Topotecan and the 22-bp DNA duplex oligonucleotide, with good geometry and no Ramachandran outliers (TABLE 4).

Both the binary Form 7 (Topo70-DNA) and ternary Form 9 (Topo70-DNA-Topotecan) complex crystals have one crystal lattice dimension that results from pseudo-continuous end-to-end packing of the 22-mer duplex DNAs. This unit cell edge is 72.0 Å in the binary complex Form 7 crystals and 75.4 Å in the ternary complex Form 9 crystals (TABLE 4). The 3.4 Å lengthening of the unit cell edge in the ternary complex is due to intercalative binding of Topotecan at the site of enzyme-mediated breakage and a concomitant 3.4 Å shift of the downstream DNA. This ligand-induced conformational change in the Topo70-DNA complex is believed to be the structural basis for why the growth of the ternary Form 9 crystals requires the presence of Topotecan.

EXAMPLE 6

Co-Crystallization of Topo70-DNA Macromolecule with Sialtecan and Indeniosoquinoline The T80P#10 crystallization condition, which promotes the growth of ternary Form 9 crystals (Topo70-DNA-Topotecan) but does not promote the growth of binary Form 7 crystals (Topo70-DNA), is used to crystallize the Topo70-DNA target in complex with other compounds that intercalate at the site of topo I cleavage. For example, the sialtecan AG260, and the indeniosoquinoline MJ-II-38 (both structures shown below) are each set up in crystallization trials with Topo70 and DNA as follows.

A Combinatorial Clover Plate reservoir chamber is filled with 1.0 milliliter T80P #10 (10% w/v PEG 8000, 100 mM ADA/NaOH pH 6.5, 200 mM Li2SO4). The surrounding drop chambers receive 2 microliters of T80P#10, 1.5 microliter of 0.05 mM suicide duplex substrate, 0.5 microliter of 1 mM AG260 in 100% DMSO or 0.3 microliter of 1 mM MJ-II-38 in 90% v/v DMSO, and 1.5 microliter of purified Topo70 at 4 mg/ml in 10 mM Tris-HCl pH 7.5, 1 mM EDTA, and 1 mM DTT. After incubation at 16° C. for several days and partial evaporation of the crystallization drop, hexagonal shaped block-like crystals grow in the presence of AG260, and plate like crystals grew in the presence of MJ-II-38.

X-ray diffraction data is collected for both crystals and their structures is solved by molecular replacement methods with AMORE [Navaza] by using the previously determined structure of the ternary Topo70-DNA-Topotecan structure (with Topotecan removed from the model) [Stewart et al., 1998]. The DNA is placed into the electron density of sigma-a weighted phase-combined maps and rigid body refined using CNX. The models are rebuilt and refined by CNX with torsion angle simulated annealing [Brunger et al.], restrained B-factor refinement, and iterative model adjustments with XtalView [McRee]. The AG260 and MJ-II-38 are placed unambiguously into the sigma-a weighted |Fobs|-|Fcalc| maps.

The crystallographic parameters for both the Topo70-DNA-AG260 and Topo70-DNA-MJ-II-38 ternary complexes reveal ~75 Angstrom unit cell edges which are the result of pseudo-continuous end-to-end DNA packing and intercalative drug binding in the crystal lattice.

The unit crystallographic parameters for the Topo70-DNA-AG260 complex are shown in Table 5. The unit crystallographic parameters for the Topo70-DNA-MJ-II-38 complex are shown in Table 6.

These results indicate that the T80P#9 crystallization condition can specifically promote crystal growth of additional Topo70-DNA-ligand ternary complex crystals, that grow due to the ability of the two ligands to bind to the Topo70-DNA complex in an intercalative binding mode at the site of enzyme cleavage on the DNA.

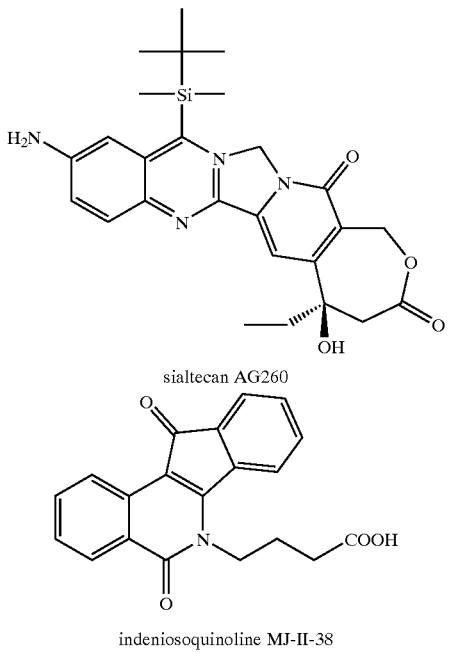

sialtecan AG260 indeniosoquinoline MJ-II-38

Exemplary embodiments of the present invention have been illustrated and described. It will be understood, however, that changes and modifications may be made to the invention without deviating from the spirit and scope of the invention, as defined by the following claims.

Tables

TABLE 1

Examples of solutions (Wizard I).

| | precipitant | buffer (0.1 M) | salt (0.2 M) |
|---|---|---|---|
| 1 | 20% (w/v) PEG-8000 | CHES pH 9.5 | none |
| 2 | 10% (v/v) 2-propanol | HEPES pH 7.5 | NaCl |
| 3 | 15% (v/v) ethanol | CHES pH 9.5 | none |
| 4 | 35% (v/v) 2-methyl-2,4-pentanediol | imidazole pH 8.0 | MgCl$_2$ |
| 5 | 30% (v/v) PEG-400 | CAPS pH 10.5 | none |
| 6 | 20% (w/v) PEG-3000 | citrate pH 5.5 | none |
| 7 | 10% (w/v) PEG-8000 | MES pH 6.0 | Zn(OAc)$_2$ |
| 8 | 2.0 M (NH$_4$)$_2$SO$_4$ | citrate pH 5.5 | none |
| 9 | 1.0 M (NH$_4$)$_2$HPO$_4$ | acetate pH 4.5 | none |
| 10 | 20% (w/v) PEG-2000 MME | Tris pH 7.0 | none |
| 11 | 20% (v/v) 1,4-butanediol | MES pH 6.0 | Li$_2$SO$_4$ |
| 12 | 20% (w/v) PEG-1000 | imidazole pH 8.0 | Ca(OAc)$_2$ |
| 13 | 1.26 M (NH$_4$)$_2$SO$_4$ | cacodylate pH 6.5 | none |
| 14 | 1.0 M sodium citrate | cacodylate pH 6.5 | none |
| 15 | 10% (w/v) PEG-3000 | imidazole pH 8.0 | Li$_2$SO$_4$ |
| 16 | 2.5 M NaCl | Na/K phosphate pH 6.2 | none |

TABLE 1-continued

Examples of solutions (Wizard I).

| | precipitant | buffer (0.1 M) | salt (0.2 M) |
|---|---|---|---|
| 17 | 30% (w/v) PEG-8000 | acetate pH 4.5 | Li$_2$SO$_4$ |
| 18 | 1.0 M K/Na tartrate | imidazole pH 8.0 | NaCl |
| 19 | 20% (w/v) PEG-1000 | Tris pH 7.0 | none |
| 20 | 0.4 M NaH$_2$PO$_4$/1.6 M K$_2$HPO$_4$ | imidazole pH 8.0 | NaCl |
| 21 | 20% (w/v) PEG-8000 | HEPES pH 7.5 | none |
| 22 | 10% (v/v) 2-propanol | Tris pH 8.5 | none |
| 23 | 15% (v/v) ethanol | imidazole pH 8.0 | MgCl$_2$ |
| 24 | 35% (v/v) 2-methyl-2,4-pentanediol | Tris pH 7.0 | NaCl |
| 25 | 30% (v/v) PEG-400 | Tris pH 8.5 | MgCl$_2$ |
| 26 | 10% (w/v) PEG-3000 | CHES pH 9.5 | none |
| 27 | 1.2 M NaH$_2$PO$_4$/0.8 M K$_2$HPO$_4$ | CAPS pH 10.5 | Li$_2$SO$_4$ |
| 28 | 20% (w/v) PEG-3000 | HEPES pH 7.5 | NaCl |
| 29 | 10% (w/v) PEG-8000 | CHES pH 9.5 | NaCl |
| 30 | 1.26 M (NH$_4$)$_2$SO$_4$ | acetate pH 4.5 | NaCl |
| 31 | 20% (w/v) PEG-8000 | phosphate-citrate pH 4.2 | NaCl |
| 32 | 10% (w/v) PEG-3000 | Na/K phosphate pH 6.2 | none |
| 33 | 2.0 M (NH$_4$)$_2$SO$_4$ | CAPS pH 10.5 | Li$_2$SO$_4$ |
| 34 | 1.0 M (NH$_4$)$_2$HPO$_4$ | imidazole pH 8.0 | none |
| 35 | 20% (v/v) 1,4-butanediol | acetate pH 4.5 | none |
| 36 | 1.0 M sodium citrate | imidazole pH 8.0 | none |
| 37 | 2.5 M NaCl | imidazole pH 8.0 | none |
| 38 | 1.0 M K/Na tartrate | CHES pH 9.5 | Li$_2$SO$_4$ |
| 39 | 20% (w/v) PEG-1000 | phosphate-citrate pH 4.2 | Li$_2$SO$_4$ |
| 40 | 10% (v/v) 2-propanol | MES pH 6.0 | Ca(OAc)$_2$ |
| 41 | 30% (w/v) PEG-3000 | CHES pH 9.5 | none |
| 42 | 15% (v/v) ethanol | Tris pH 7.0 | none |
| 43 | 35% (v/v) 2-methyl-2,4-pentanediol | Na/K phosphate pH 6.2 | none |
| 44 | 30% (v/v) PEG-400 | acetate pH 4.5 | Ca(OAc)$_2$ |
| 45 | 20% (w/v) PEG-3000 | acetate pH 4.5 | none |
| 46 | 10% (w/v) PEG-8000 | imidazole pH 8.0 | Ca(OAc)$_2$ |
| 47 | 1.26 M (NH$_4$)$_2$SO$_4$ | Tris pH 8.5 | Li$_2$SO$_4$ |
| 48 | 20% (w/v) PEG-1000 | acetate pH 4.5 | Zn(OAc)$_2$ |

All formulations are preferably made with ultrapure ASTM Type I water, and sterile-filtered into sterile tubes. Store at 4–25° C.

TABLE 2

Examples of solutions (Wizard II).

| | precipitant | buffer (0.1 M) | salt (0.2 M) |
|---|---|---|---|
| 1 | 10% (w/v) PEG-3000 | acetate pH 4.5 | Zn(OAc)$_2$ |
| 2 | 35% (v/v) 2-methyl-2,4-pentanediol | MES pH 6.0 | Li$_2$SO$_4$ |
| 3 | 20% (w/v) PEG-8000 | Tris pH 8.5 | MgCl$_2$ |
| 4 | 2.0 M (NH$_4$)$_2$SO$_4$ | cacodylate pH 6.5 | NaCl |
| 5 | 20% (v/v) 1,4-butanediol | HEPES pH 7.5 | NaCl |
| 6 | 10% (v/v) 2-propanol | phosphate-citrate pH 4.2 | Li$_2$SO$_4$ |
| 7 | 30% (w/v) PEG-3000 | Tris pH 7.0 | NaCl |
| 8 | 10% (w/v) PEG-8000 | Na/K phosphate pH 6.2 | NaCl |
| 9 | 2.0 M (NH$_4$)$_2$SO$_4$ | phosphate-citrate pH 4.2 | none |
| 10 | 1.0 M (NH$_4$)$_2$HPO$_4$ | Tris pH 8.5 | none |
| 11 | 10% (v/v) 2-propanol | cacodylate pH 6.5 | Zn(OAc)$_2$ |
| 12 | 30% (v/v) PEG-400 | cacodylate pH 6.5 | Li$_2$SO$_4$ |
| 13 | 15% (v/v) ethanol | citrate pH 5.5 | Li$_2$SO$_4$ |

TABLE 2-continued

Examples of solutions (Wizard II).

| | precipitant | buffer (0.1 M) | salt (0.2 M) |
|---|---|---|---|
| 14 | 20% (w/v) PEG-1000 | Na/K phosphate pH 6.2 | NaCl |
| 15 | 1.26 M (NH$_4$)$_2$SO$_4$ | HEPES pH 7.5 | none |
| 16 | 1.0 M sodium citrate | CHES pH 9.5 | none |
| 17 | 2.5 M NaCl | Tris pH 7.0 | MgCl$_2$ |
| 18 | 20% (w/v) PEG-3000 | Tris pH 7.0 | Ca(OAc)$_2$ |
| 19 | 1.6 M NaH$_2$PO$_4$/0.4 M K$_2$HPO$_4$ | phosphate-citrate pH 4.2 | none |
| 20 | 15% (v/v) ethanol | MES pH 6.0 | Zn(OAc)$_2$ |
| 21 | 35% (v/v) 2-methyl-2,4-pentanediol | acetate pH 4.5 | none |
| 22 | 10% (v/v) 2-propanol | imidazole pH 8.0 | none |
| 23 | 15% (v/v) ethanol | HEPES pH 7.5 | MgCl$_2$ |
| 24 | 30% (w/v) PEG-8000 | imidazole pH 8.0 | NaCl |
| 25 | 35% (v/v) 2-methyl-2,4-pentanediol | HEPES pH 7.5 | NaCl |
| 26 | 30% (v/v) PEG-400 | CHES pH 9.5 | none |
| 27 | 10% (w/v) PEG-3000 | cacodylate pH 6.5 | MgCl$_2$ |
| 28 | 20% (w/v) PEG-8000 | MES pH 6.0 | Ca(OAc)$_2$ |
| 29 | 1.26 M (NH$_4$)$_2$SO$_4$ | CHES pH 9.5 | NaCl |
| 30 | 20% (v/v) 1,4-butanediol | imidazole pH 8.0 | Zn(OAc)$_2$ |
| 31 | 1.0 M sodium citrate | Tris pH 7.0 | NaCl |
| 32 | 20% (w/v) PEG-1000 | Tris pH 8.5 | none |
| 33 | 1.0 M (NH$_4$)$_2$HPO$_4$ | citrate pH 5.5 | NaCl |
| 34 | 10% (w/v) PEG-8000 | imidazole pH 8.0 | none |
| 35 | 0.8 M NaH$_2$PO$_4$/1.2 M K$_2$HPO$_4$ | acetate pH 4.5 | none |
| 36 | 10% (w/v) PEG-3000 | phosphate-citrate pH 4.2 | NaCl |
| 37 | 1.0 M K/Na tartrate | Tris pH 7.0 | Li$_2$SO$_4$ |
| 38 | 2.5 M NaCl | acetate pH 4.5 | Li$_2$SO$_4$ |
| 39 | 20% (w/v) PEG-8000 | CAPS pH 10.5 | NaCl |
| 40 | 20% (w/v) PEG-3000 | imidazole pH 8.0 | Zn(OAc)$_2$ |
| 41 | 2.0 M (NH$_4$)$_2$SO$_4$ | Tris pH 7.0 | Li$_2$SO$_4$ |
| 42 | 30% (v/v) PEG-400 | HEPES pH 7.5 | NaCl |
| 43 | 10% (w/v) PEG-8000 | Tris pH 7.0 | MgCl$_2$ |
| 44 | 20% (w/v) PEG-1000 | cacodylate pH 6.5 | MgCl$_2$ |
| 45 | 1.26 M (NH$_4$)$_2$SO$_4$ | MES pH 6.0 | none |
| 46 | 1.0 M (NH$_4$)$_2$HPO$_4$ | imidazole pH 8.0 | NaCl |
| 47 | 2.5 M NaCl | imidazole pH 8.0 | Zn(OAc)$_2$ |
| 48 | 1.0 M K/Na tartrate | MES pH 6.0 | none |

All formulations are made with ultrapure ASTM Type I water, and sterile-filtered into sterile tubes. Store at room temperature.

TABLE 3

CBS-cross crystallization solutions.

| Designation | Crystallants | Buffers and Salts |
|---|---|---|
| T80P #1 | 10% w/v PEG 8000 | 100 mM Citrate/citric acid pH 5.5, 200 mM NaCl |
| T80P #2 | 10% w/v PEG 8000 | 100 mM Na2 H/K H2 phosphate pH 6.2, 200 mM NaCl |
| T80P #3 | 10% w/v PEG 8000 | 100 mM MES/NaOH pH 6.4, 200 mM NaCl |
| T80P #4 | 10% w/v PEG 8000 | 100 mM ADA/NaOH pH 6.5, 200 mM NaCl |
| T80P #5 | 10% w/v PEG 8000 | 100 mM Tris/HCl pH 7.0, 200 mM NaCl |
| T80P #6 | 10% w/v PEG 8000 | 100 mM Tris/HCl pH 8.5, 200 mM NaCl |
| T80P #7 | 10% w/v PEG 8000 | 100 mM Citrate/citric acid pH 5.5, 200 mM Li$_2$SO$_4$ |
| T80P #8 | 10% w/v PEG 8000 | 100 mM Na2 H/K H2 phosphate pH 6.2, 200 mM Li$_2$SO$_4$ |

TABLE 3-continued

CBS-cross crystallization solutions.

| Designation | Crystallants | Buffers and Salts |
|---|---|---|
| T80P #9 | 10% w/v PEG 8000 | 100 mM MES/NaOH pH 6.4, 200 mM Li$_2$SO$_4$ |
| T80P #10 | 10% w/v PEG 8000 | 100 mM ADA/NaOH pH 6.5, 200 mM Li$_2$SO$_4$ |
| T80P #11 | 10% w/v PEG 8000 | 100 mM Tris/HCl pH 7.0, 200 mM Li$_2$SO$_4$ |
| T80P #12 | 10% w/v PEG 8000 | 100 mM Tris/HCl pH 8.5, 200 mM Li$_2$SO$_4$ |
| T80P #13 | 10% w/v PEG 8000 | 100 mM Citrate/citric acid pH 5.5, 200 mM KCl |
| T80P #14 | 10% w/v PEG 8000 | 100 mM Na2 H/K H2 phosphate pH 6.2, 200 mM KCl |
| T80P #15 | 10% w/v PEG 8000 | 100 mM MES/NaOH pH 6.4, 200 mM KCl |
| T80P #16 | 10% w/v PEG 8000 | 100 mM ADA/NaCH pH 6.5, 200 mM KCl |
| T80P #17 | 10% w/v PEG 8000 | 100 mM Tris/HCl pH 7.0, 200 mM KCl |
| T80P #18 | 10% w/v PEG 8000 | 100 mM Tris/HCl pH 8.5, 200 mM KCl |
| T80P #19 | 10% w/v PEG 8000 | 100 mM Citrate/citric acid pH 5.5, 200 mM Na2 H/K H2 phosphate pH 6.2 |
| T80P #20 | 10% w/v PEG 8000 | 100 mM Na2 H/K H2 phosphate pH 6.2, 200 mM Na2 H/K H2 phosphate pH 6.2 |
| T80P #21 | 10% w/v PEG 8000 | 100 mM MES/NaOH pH 6.4, 200 mM Na2 H/K H2 phosphate pH 6.2 |
| T80P #22 | 10% w/v PEG 8000 | 100 mM ADA/NaOH pH 6.5, 200 mM Na2 H/K H2 phosphate pH 6.2 |
| T80P #23 | 10% w/v PEG 8000 | 100 mM Tris/HCl pH 7.0, 200 mM Na2 H/K H2 phosphate pH 6.2 |
| T80P #24 | 10% w/v PEG 8000 | 100 mM Tris/HCl pH 8.5, 200 mM Na2 H/K H2 phosphate pH 6.2 |

TABLE 4

Refinement Statistics.

| CRYSTAL FORM | FORM 9 | FORM 7 |
|---|---|---|
| Inhibitor bound | Topotecan | — |
| Resolution (Å) | 2.1 | 3.2 |
| No. reflections | 46866 | 17874 |
| Rsym[a] | 6.2 | 13.0 |
| Completeness | 81.1 | 85.9 |
| Space Group | P2$_1$ | P3(2) |
| a | 57.093 Å | 73.235 |
| b | 116.620 Å | 73.235 |
| c | 75.213 Å | 186.632 |
| β | 94.156 | — |
| Reflections used in RFREE | 10% | 10% |
| No. of protein atoms | 4685 | 3498 |
| No. of DNA atoms | 892 | 892 |
| No. of inhibitor atoms | 31 | — |
| No. of solvent atoms | 234 | — |
| RFACTOR | 23.4 | 21.7[b] |
| RFREE | 27.4 | 28.4[b] |
| r.m.s. deviations from ideal stereochemistry | | |
| bond lengths (Å) | 0.0068 | 0.0088 |
| bond angles (°) | 1.17 | 1.36 |
| dihedrals (°) | 21.3 | 22.16 |
| impropers (°) | 3.6 | 3.35 |
| Mean Bfactor –all atoms (Å$^3$) | 39.3 | 41.8 |

[a]Rsym = $\Sigma |I_i - I_m|/\Sigma I_m$ where $I_i$ is the intensity of the measured reflection and $I_m$ is the mean intensity of all symmetry related reflections.
[b]Non-drug bound crystals were merohedrally twinned (twin law h, –h – k, –l; twin fraction = 0.151 estimated using CNX). R factors were calculated using twinned data.

TABLE 5

The unit crystallographic parameters for the Topo70-DNA-AG260 complex.

| Resolution: | 3.0 Angstrom |
|---|---|
| R-factor: | 21.3 |
| R-free: | 29.2 |
| Space Group: | P21 |
| Cell edge a: | 57.357 |
| Cell edge b: | 115.977 |
| Cell edge c: | 74.998 |
| Angle Alpha: | 90 |
| Angle Beta: | 97.2 |
| Angle Gamma: | 90 |

TABLE 6

The unit crystallographic parameters for the Topo70-DNA-MJ-II-38 complex.

| Resolution: | 3.0 Angstrom |
|---|---|
| R-factor: | 21.3 |
| R-free: | 27.1 |
| Space Group: | C2 |
| Cell edge a: | 260.94 |
| Cell edge b: | 74.659 |
| Cell edge c: | 57.494 |
| Angle Alpha: | 90 |
| Angle Beta: | 96.939 |
| Angle Gamma: | 90 |

References

Carter D C, Miller T Y: Protein crystal growth tray assembly. U.S. Pat. No. 1992, 5,130,105.

Kim H, Stewart L J: Crystallization tray. U.S. Pat. No. 2000, 6,039,804.

Hol W G J, Sarfaty S H, Stewart L J, Kim H: Crystallization media. U.S. Pat. No. 2001, 6,267,935.

Bernstein B E, Michels P A, Hol W G: Synergistic effects of substrate-induced conformational changes in phosphoglycerate kinase activation. Nature 1997, 385:275–278.

Bernstein B E, Williams D M, Bressi J C, Kuhn P, Gelb M H, Blackburn G M, Hol W G: A bisubstrate analog induces unexpected conformational changes in phosphoglycerate kinase from *Trypanosoma brucei*. J Mol Biol 1998, 279:1137–1148.

Scapin G, Patel S, Patel V, Kennedy B, Asante-Appiah E: The structure of apo protein-tyrosine phosphatase 1B C215S mutant: more than just an S —>O change. Protein Sci 2001, 10:1596–1605.

Jia Z, Ye Q, Dinaut A N, Wang Q, Waddleton D, Payette P, Ramachandran C, Kennedy B, Hum G, Taylor S D:

Structure of protein tyrosine phosphatase 1B in complex with inhibitors bearing two phosphotyrosine mimetics. J Med Chem 2001, 44:4584–4594.

Huang H, Chopra R, Verdine G L, Harrison S C: Structure of a covalently trapped catalytic complex of HIV-1 reverse transcriptase: implications for drug resistance. Science 1998, 282:1669–1675.

Champoux J J: DNA Topoisomerases: structure, function, and mechanism. Ann. Rev. Biochem. 2001, 70:369–413.

Wall M E, Wani M C, Cook C E, Palmer K H, McPhail A T, Sim G A: The isolation and structure of camptothecin, a novel alkaloidal leukemia and tumor inhibitor from *Camptotheca acuminata*. J. Am. Chem. Soc. 1966, 88:3888–3890.

Nitiss J L, Wang J C: DNA topoisomerase-targeting antitumor drugs can be studied in yeast. Proc. Natl. Acad. Sci. U.S.A. 1988, 85:7501–7505.

Hsiang Y H, Hertzberg R, Hecht S, Liu L F: Camptothecin induces protein-linked DNA breaks via mammalian DNA topoisomerase I. J. Biol. Chem. 1985, 260:14873–14878.

Hertzberg R P, Caranfa M J, Hecht S M: On the mechanism of topisomerase I inhibition by camptothecin: evidence for binding to an enzyme-DNA complex. Biochem. 1989, 28:4629–4638.

Chen A Y, Liu L F: DNA topoisomerases: Essential enzymes and lethal targets. Rev. Pharmacol. Toxicol. 1994, 34:191–218.

Stewart L, Ireton G C, Parker L H, Madden K R, Champoux J J: Biochemical and biophysical analyses of recombinant forms of human topoisomerase I. J Biol Chem 1996, 271:7593–7601.

Burgin A B, Jr., Huizenga B N, Nash H A: A novel suicide substrate for DNA topoisomerases and site-specific recombinases. Nucleic Acids Res 1995, 23:2973–2979.

Redinbo M R, Stewart L, Kuhn P, Champoux J J, Hol W G: Crystal structures of human topoisomerase I in covalent and noncovalent complexes with DNA. Science 1998, 279:1504–1513.

Hampton Research Solutions for Crystal Growth, Crystal Screen Reagent Formulations, listing PDF, 3pp, Downloaded from Hampton Research Website http://www.hamptonresearch.com/hrproducts/2110.html on World Wide Web URL: http://www.hamptonresearch.com/hrproducts/2110.html Stewart L, Clark R, Behnke C: High-throughput crystallization and structure determination in drug discovery. Drug Discov Today 2002, 7:187–196.

Navaza J: AMORE: an automated package for molecular replacement. Acta. Crystallogr. 1994, A50:157–163.

Stewart L, Redinbo M R, Qiu X, Hol W G, Champoux J J: A model for the mechanism of human topoisomerase I. Science 1998, 279:1534–1541.

Brünger A T, et al.: Crystallography and NMR systems (CNS): A new software system for macromolecular structure determination. Acta. Crystallogr. 1998, D54:905–921.

McRee D E: XtalView/Xfit—A Versatile Program for Manipulating Atomic Coordinates and Electron Density. J. Struct. Biol. 1999, 125:156–165.

Stewart L, Ireton G C, Champoux J J: Reconstitution of human topoisomerase I by fragment complementation. J Mol Biol 1997, 269:355–372.

What is claimed is:

1. A process for identifying a ligan which binds to a protein/nucleic acid co-complex comprising:
providing a solution containing a protein/nucleic acid co-complex;
exposing the solution to a potential ligand under conditions wherein the co-complex forms crystals only when bound to a ligand; and observing whether crystallization of the protein/nucleic acid co-complex occurs, wherein the protein/nucleic acid co-complex forms crystals only when bound to a ligand, and wherein formation of crystals indicates binding between the protein/nucleic acid co-complex and the potential ligand.

2. The process of claim 1 wherein said observing step is conducted visually.

3. The process of claim 1 wherein said observing step is conducted with a microscope.

4. The process of claim 1 wherein the potential ligand is a single strand nick specific compound.

5. The process of claim 1 wherein protein/nucleic acid co-complex is a complex of a topoisomerase and a suicide substrate.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (10)..(11)
<223> OTHER INFORMATION: 5' bridging phosphorothiolate linkage

<400> SEQUENCE: 1
aaaaagactt tgaaaaattt tt                                              22

<210> SEQ ID NO 2
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 2
tttttctgaa actttttaaa aa                                              22
```